United States Patent
Burnett

(10) Patent No.: US 6,850,637 B1
(45) Date of Patent: Feb. 1, 2005

(54) LIGHTING ARRANGEMENT FOR AUTOMATED OPTICAL INSPECTION SYSTEM

(75) Inventor: John B. Burnett, Vacaville, CA (US)

(73) Assignee: Teradyne, Inc., Boston, MA (US)

( * ) Notice: Subject to any disclaimer, the term of this patent is extended or adjusted under 35 U.S.C. 154(b) by 607 days.

(21) Appl. No.: 09/605,354

(22) Filed: Jun. 28, 2000

(51) Int. Cl.$^7$ ................................................. G06K 9/00
(52) U.S. Cl. .................. 382/147; 250/559.08; 348/126; 356/237
(58) Field of Search ................................. 382/312, 317, 382/321, 141–152; 356/237, 356, 359, 348, 384, 395, 372, 237.1; 348/131, 126, 135; 359/387, 385, 388, 613; 250/559.08, 205; 235/462.42, 462.43, 462.44

(56) References Cited

U.S. PATENT DOCUMENTS

| | | | |
|---|---|---|---|
| 4,682,040 A | | 7/1987 | Hohki et al. ............... 250/571 |
| 4,893,223 A | * | 1/1990 | Arnold ..................... 356/237.1 |
| 5,010,412 A | | 4/1991 | Garriss ....................... 358/240 |
| 5,060,065 A | * | 10/1991 | Wasserman ................. 348/131 |
| 5,245,421 A | | 9/1993 | Robertson et al. .......... 358/101 |
| 5,309,277 A | * | 5/1994 | Deck .......................... 250/205 |
| 5,349,172 A | * | 9/1994 | Roustaei ................ 235/462.42 |
| 5,365,084 A | * | 11/1994 | Cochran et al. ....... 250/559.02 |
| 5,690,417 A | * | 11/1997 | Polidor et al. .............. 359/387 |
| 5,822,053 A | | 10/1998 | Thraikill .................... 356/237 |
| 6,457,645 B1 | * | 10/2002 | Gardner, Jr. ........... 235/462.23 |

FOREIGN PATENT DOCUMENTS

WO    WO 99/44409    9/1999    .......... H05K/13/08

OTHER PUBLICATIONS

Patents Abstracts of Japan; vol. 2000, No. 01; Jan. 31, 2000 & JP 11 295047 A, Oct. 29, 1998; figure 5, col. 4, line 26–line 64.

*Model 5511A Automatic Loaded PC Board Inspection System* Brochure published by Universal Instruments Corporation, dated 1987.

\* cited by examiner

*Primary Examiner*—Jayanti K. Patel
(74) *Attorney, Agent, or Firm*—Edmund J. Walsh; Teradyne Legal Dept.

(57) ABSTRACT

An optical inspection system with an improved illumination system. The improved illumination system used to illustrate the invention has a base formed from a printed circuit board. Substrates for mounting lighting elements, which are exemplified by light emitting diodes, are formed also on printed circuit boards. These circuit boards have serrated edges and the diodes are mounted to the serrations. This configuration allows the light emitting elements to be focused on the focal point. Also in the exemplary illumination system, the light emitting elements have different beam widths so that variations in the illumination intensity as a function of elevation angle are reduced.

16 Claims, 3 Drawing Sheets

LIGHTING ARRANGEMENT FOR AUTOMATED OPTICAL INSPECTION SYSTEM

This invention relates generally to automated optical inspection systems and more specifically to the lighting arrangement for such inspection systems.

Automated optical inspection is used during the manufacture of printed circuit boards and in other fields. A computer controlled system passes a camera over the printed circuit board or other object being inspected and takes images of various regions on the board. The images are then scanned by the computer to verify that features expected to be present in a properly manufactured board are in that region and have an expected shape. Alternatively, the system might verify that there are no features in that region that should not be present. If the features are verified, the board passes inspection. If they are not verified, the board is either labeled as defective or passed on for human inspection or additional testing.

When the object being inspected in a printed circuit board, the features of interest will be things such as edges of electronic components, metal traces or solder. Many of these features will be captured in an image, though, only if the light strikes the object at a certain angle relative to the camera that is forming the image. For example, if the object has a shiny surface that is oriented to reflect light away from the camera, the camera will capture no light from the object. If the camera captures no light reflecting from the object, the area where the object is will appear black in the image formed by the camera.

Thus, to create an image that is useful for automated inspection, the lighting of the inspection area must be controlled relative to the cameras. Some automated inspection system use annular light sources that provide light from all around the area being inspected. However, these types of light sources had several drawbacks. First, annular light sources generally allowed a camera to be focused on the inspection area only from the top looking through the annulus from a direction perpendicular to the printed circuit board. Often, features on a board being inspected will not be readily apparent in an image taken from this direction.

Often, various "lighting modes" are desired to take multiple images of the same area under inspection. In each lighting mode, the area under inspection is illuminated from a different angle or a different combination of angles.

Annular light sources are known. Some such sources have been made with arrays of light emitting diodes. When the light emitting diodes are operated in sectors, the inspection area can be illuminated from different directions. When the light emitting diodes are operated in groups based on their distance from the center of the annulus, the inspection area can be illuminated from different elevation angles. Lighting from different elevation angles is useful in highlighting different kinds of features on the printed circuit boards. The drawback of annular lighting systems, though, is that the light emitting elements that are used to illuminate the inspection area from a low elevation angle are further from the inspection area than those light emitting elements used to illuminate the inspection area at a high elevation angle. Additionally, the illumination area is further from the center of the beam for light emitting elements at the periphery of the annulus. Consequently, the inspection area is illuminated at a lower intensity when lighting from a low elevation angle is required. Such variations in lighting intensity are not desirable for an inspection system.

U.S. Pat. No. 5,245,421 shows a lighting apparatus for inspecting printed circuit boards with surface mounted components that is better suited for providing multiple lighting modes. FIG. 1 of that patent is reproduced as FIG. 1 herein. FIG. 1 shows a portion of the inspection apparatus 10. Apparatus 10 contains an inspection head 12.

Inspection head 12 is mounted on an X-Y table 13 so that it may be moved over the surface of a printed circuit board to be inspected. The remainder of the apparatus is not shown, but it includes mechanical structures to move printed circuit boards into and out of an inspection area under X-Y table 13 and other conventional components of an inspection, such as a computer controller.

Inspection head 12 includes cameras that acquire images of the board. In the illustrated embodiment, four cameras 14, 15, 16 and 17 are shown. The cameras 14, 15, 16 and 17 are mounted in a hollow cylinder 30 with an open bottom 31. Inside cylinder 31 are mounted light groups, of which 23 and 24 are visible in FIG. 1. However, the patent describes that there are four light groups inside cylinder 30. The light groups can be operated singly or in combination to provide various lighting modes at the open bottom 31. In use, open bottom 31 is placed near the printed circuit board under inspection and centered over the area being inspected. That area is lighted from various angles by selective activation of the light groups and images are formed of components on the board using the cameras.

U.S. Pat. No. 5,060,065 describes the lights inside cylinder 30 in greater detail. That patent describes that the light groups are formed from arrays of light emitting diodes distributed around the surface of a dome inside cylinder 30. In a commercial embodiment of the lighting apparatus pictured in U.S. Pat. No. 5,060,065, identical diodes are mounted to curved printed circuit boards that are soldered to a ring. In this way, each light emitting diode is essentially the same distance from the inspection area near open bottom 31. Further, the beam center of each light emitting diode is focused on the inspection area. Such an arrangement provides much greater uniformity in illumination. In addition, space between printed circuit boards carrying the light emitting diodes allowed the multiple cameras to be focused through the dome onto the inspection area.

However, to adequately illuminate components on the printed circuit board, the open bottom 31 has to be very close to the surface of the printed circuit board being inspected—roughly 1.75 mm (0.7 inches) or less. This restriction prevents the system from being used to manufacture printed circuit boards with tall components such as transformers or large value capacitors. We have invented a way to allow a light source to operate with taller components on the surface of the printed circuit board. As will be described in greater detail below, we have also invented ways to simplify the manufacture of the lighting structure.

SUMMARY OF THE INVENTION

With the foregoing background in mind, it is an object of the invention to provide an improved lighting structure for an automated optical inspection system.

The foregoing and other objects are achieved in a lighting structure having a substantially planar base and a plurality of light emitting elements supported by the base. In the preferred embodiment, the light emitting elements are diodes attached in groups to substrates projecting from the base. In the presently preferred embodiments, the base and substrates are both printed circuit boards and are interconnected with plug type connectors.

In the preferred embodiments, the substrates are mounted along lines that radiate from a common point and the light emitting elements are mounted to focus their beams at an inspection area below this common point. Another feature of the preferred embodiments is that light emitting elements mounted further from the common have a narrower beam angle than the light emitting elements mounted closer to the common point. Using light emitting elements with different beam angles reduces variations in the size of the area illuminated by each light emitting source and also reduces variations in beam intensity in the inspection area from light emitting elements at different distances from the inspection area.

BRIEF DESCRIPTION OF THE DRAWINGS

The invention will be better understood by reference to the following more detailed description and accompanying drawings in which.

DESCRIPTION OF THE PREFERRED EMBODIMENT

Figure 1:
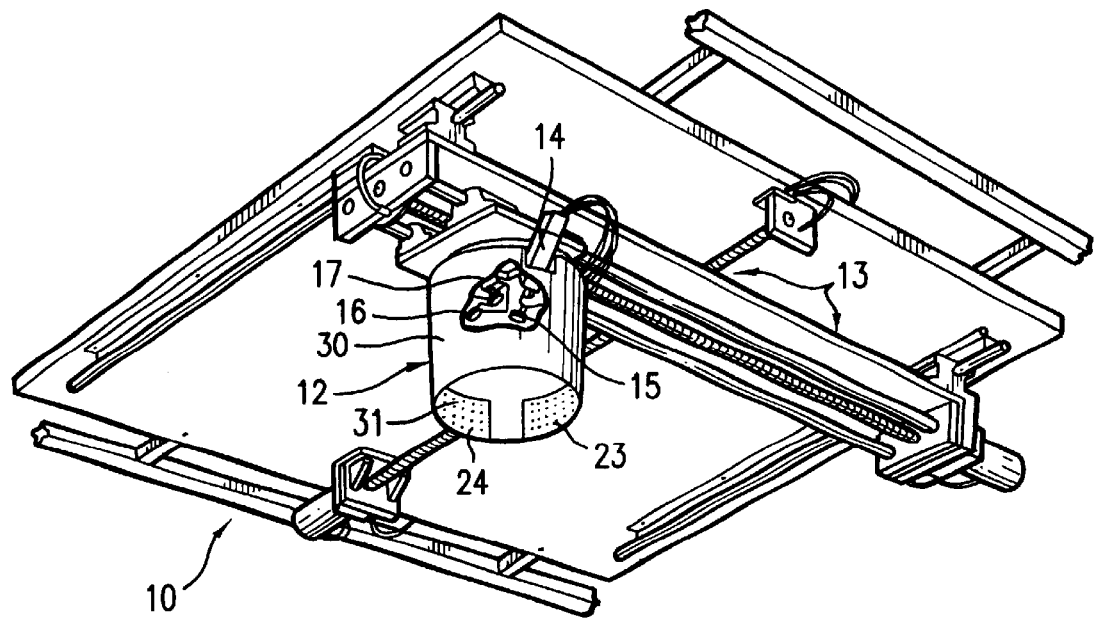
FIG. 1 is a sketch of a prior art illumination system.
Figure 2:
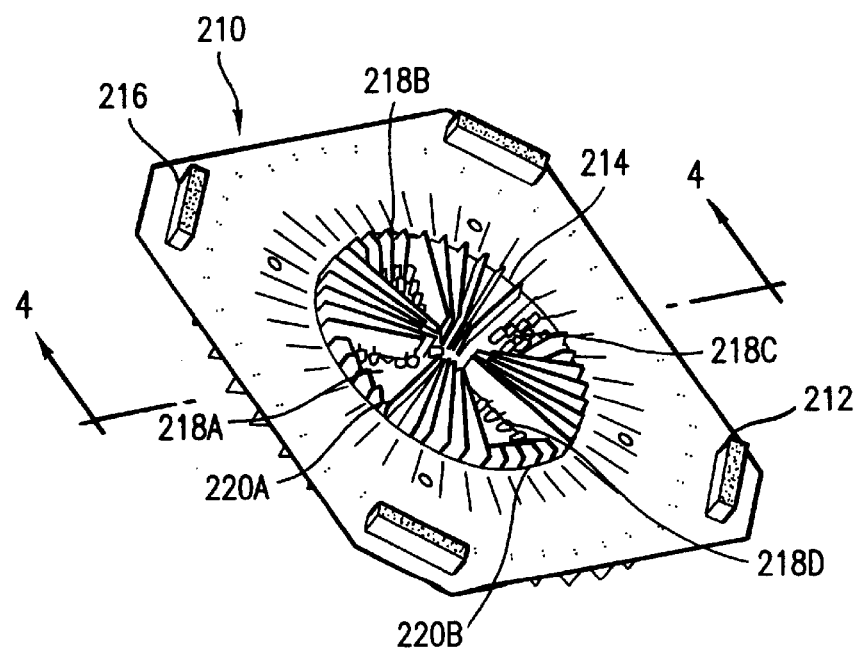
FIG. 2 is a sketch of a surface of an illumination system according to the invention.

FIG. 2 shows an illumination system 210 according to the invention. In use, illumination system 210 would be used in place of cylinder 30 in FIG. 1. In a preferred embodiment, illumination system 210 is used in an automated optical inspection system for printed circuit boards. Illumination system 210 would provide lighting on the board at various stages of its manufacture. It can be used to provide lighting for inspection of printed circuit boards with tall components such that the clearance between the illumination system 210 and the surface of the board being inspected must be 1.7 mm or more.

Such a system would be used in the manufacture of printed circuit boards. Circuit boards are often inspected at several steps during their manufacturing process. The inspection is sometimes used to alter the work flow for the individual boards. For example, if an inspection reveals a missing component on the board, the board might be re-routed for rework. The precise manner in which the system of the invention is used to alter the work flow in the manufacturing is not important to the invention.

Figure 3:
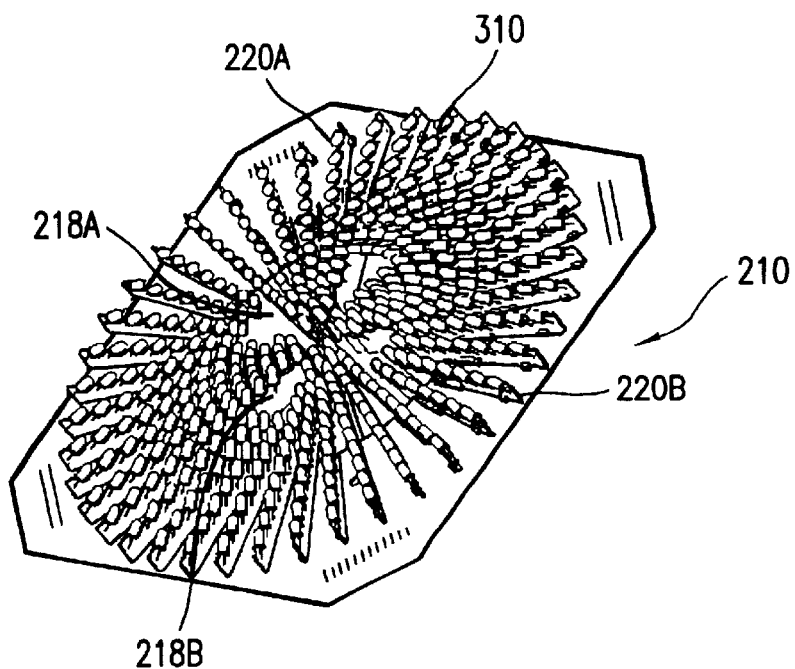
FIG. 3 is a sketch of the opposite surface of the illumination system of FIG. 2.

Illumination system 210 has a base, which in the illustrated embodiment is printed circuit board 212. Board 212 can be a conventional printed circuit board, with conductive traces in it. These traces carry the signals that control individual lighting elements 310 (FIG. 3). Electrical connectors 216, which can be traditional pin and socket type connectors, are mounted in convenient locations on board 212. In the illustrated embodiment, board 212 is generally square and connectors 216 are mounted in the corners of the board.

Board 212 also has an opening 214 in it. Opening 214 provides locations for cameras (not shown) to be focused through illumination system 210 to an inspection area on a printed circuit board under test In the illustrated embodiment, there are five such locations. There are four camera locations 218A, 218B, 218C and 218D (FIGS. 2–4) located at different angles around opening 214. There is a fifth camera location 218E (FIG. 4) in the center of opening 214. These camera locations allow cameras to form images of an inspection area from multiple angles.

Attached to board 212 are a plurality of lighting substrates. In the illustrated embodiment, lighting substrates are provided by a plurality of printed circuit boards 220a and 220b. Manufacture of boards 220a and 220b are described in greater detail below in conjunction with FIG. 5.

Both boards 220a and 220b extend into opening 214. Neither boards 220a nor 220b extend to the center of opening 214. By not extending the boards to the center of opening 214, camera location 218d is formed. In addition, boards 220a are shorter than boards 220b, extending only part way into opening 214. In this way, there are unobstructed passages through opening 214 that form camera locations 218a . . . 218d.

Boards 220a and 220b are better seen in FIG. 3, which shows that side of illumination system that would face a printed circuit board under inspection during operation of the system. Each board 220a and 22b have a plurality of lighting elements attached to them. In the preferred embodiment, the lighting elements are photodiodes. Because boards 220b are longer than boards 220a, they are shown to have more lighting elements attached to them.

In the illustrated embodiment, each of the boards 220a and 220b is attached to board 212 along a line that emanates from the center of opening 214. Lighting elements 310 are attached to boards 220a and 220b in a pattern that also generally follows the lines emanating from the center of opening 214.

Such an arrangement is useful when the center of opening 214 is aligned with the area to be inspected of a printed circuit board. In this way, lighting elements 310 are disposed in circles of varying radii around the area to be inspected. As in the prior art, the lighting elements 310 can be simultaneously activated in sectors. Activating lighting elements in one sector causes the inspection area to be illuminated from one side. Instead or in addition, only lighting elements that are a specified radius from the inspection area results in illuminating the inspection area from different elevation angles.

As shown in FIG. 3, each of the boards 220a and 220b is mounted to project from board 212. In the preferred embodiment, each of the boards 220a and 220b projects at a substantially right angle from board 212. This configuration places one edge of each board 220a and 220b against board 212 and a second edge of each board 220a and 220b generally facing the printed circuit board being inspected. These edges of boards 220a and 220b provide convenient points of attachment for electrical connectors (412a and 412b in FIG. 4) to connect each board 220a and 220b to board 212. These edges also provide convenient points of attachment for light emitting elements 310.

Traces within boards 220a and 220b run between the connectors and the lighting elements. In this way, electrical signals can be routed to the individual lighting elements. In particular, electrical signals can be routed from a system controller (not shown) through connectors 216, through traces on board 212, through connectors 412a and 412b, through traces on boards 220a and 220b to lighting elements 310. Many separate paths for separate lighting elements 310 are provided in a way that is simple to manufacture. In particular, components and connectors are soldered to printed circuit boards to create subassemblies, which are then plugged together into a finished assembly.

Figure 4:
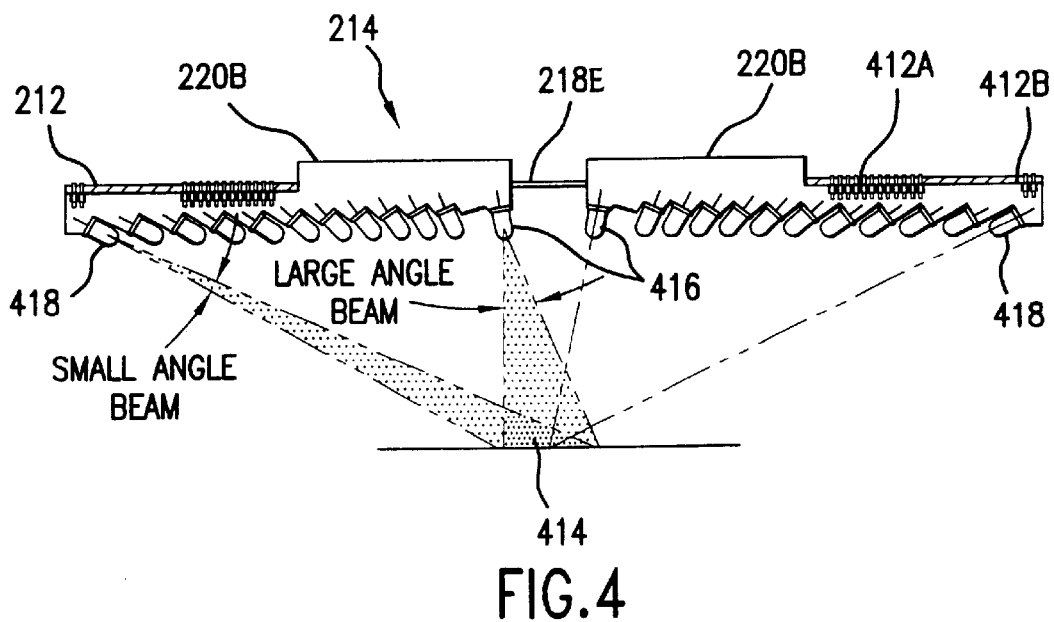
FIG. 4 is a cross sectional view of through the illumination system taken through the line 4—4 in FIG. 2.

Turning to FIG. 4, a cross section of illumination system 210 is shown taken along the line 4—4 in FIG. 2. In this view, two boards 220b are visible. The connectors 412a and 412b are shown as are lighting elements 310. As seen in FIG. 4, each of the lighting elements 310 is mounted to direct its beam at an inspection area, which in this embodiment falls below the center of opening 214. With the light emitting diodes used in the preferred embodiment, to direct the beams in this fashion, it is necessary that each of the light emitting diodes be mounted at a different angle.

Figure 5:
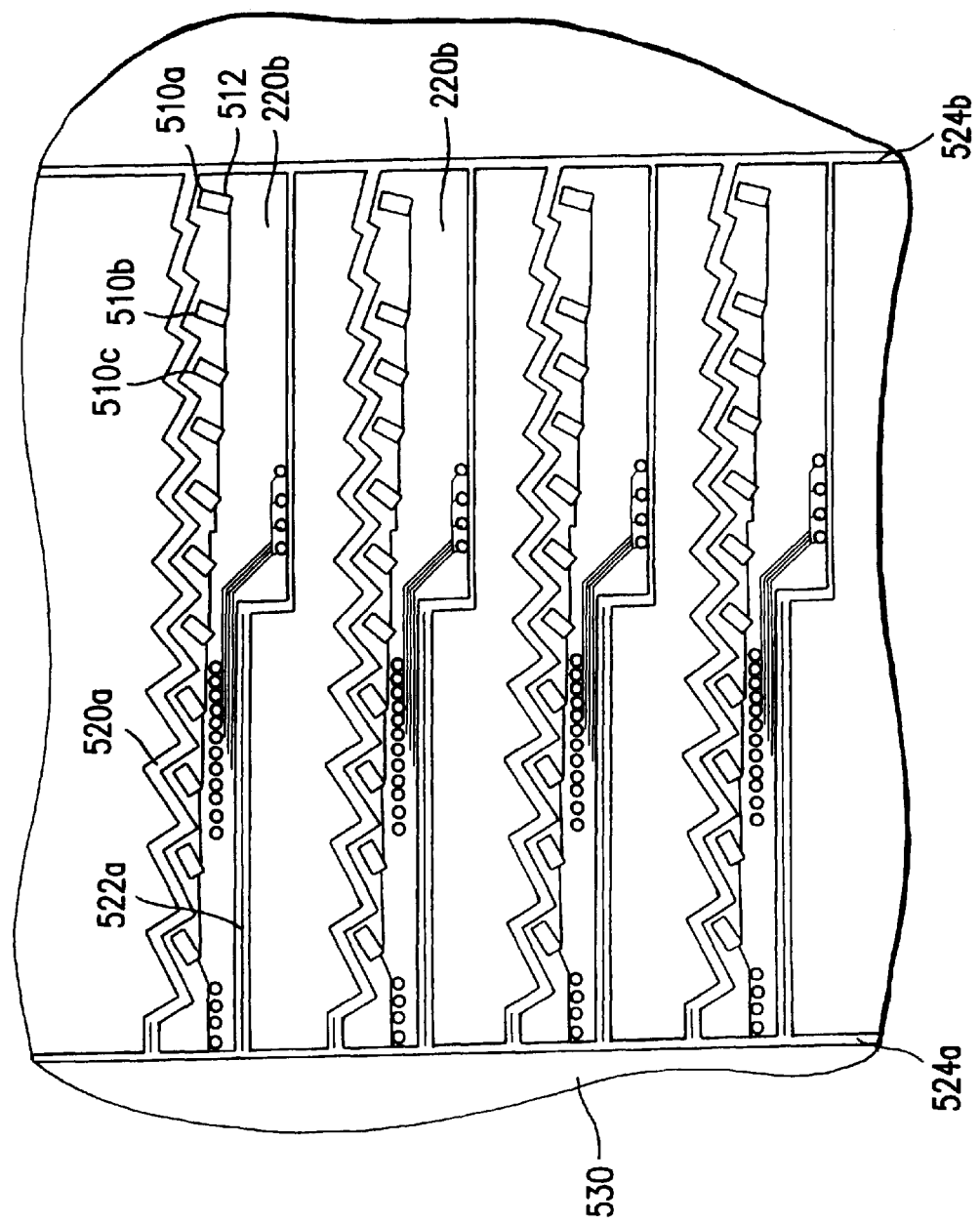
FIG. 5 is a sketch of printed circuit boards used to form the illumination system of FIG. 2.

In the preferred embodiment, the light emitting diodes are mounted at different angles by first forming platforms (of which some are numbered 510a . . . 510c for illustration in FIG. 5) along the edge of boards 220a and 220b. As shown in FIG. 5, conducting pads are formed on the platforms (such as those numbered 510a . . . 510c) to which leads of the light emitting diodes may be soldered or attached using any convenient mechanism. The platforms give the edges of printed circuit boards 220a and 220b a serrated appearance. The orientation of the platform is selected to point the lighting element at the illumination area. This pattern could be termed a Fresnel pattern.

In the preferred embodiment, the light emitting elements on each board 220b are not the same. Those light emitting diodes 416 mounted closer to the inspection area 414 have a wider beam angle that those light emitting diodes 418 that are mounted furthest from the inspection area 414. In this way, the intensity at the inspection area 414 is equalized. While theoretically each lighting element on each board 220b could have a different beam angle, there are practical limits to the beam angles that are readily available. In one embodiment, only two different types of light emitting diodes are used, with the one having the closest beam angle to what is desired for a particular location being selected.

Turning now to FIG. 5, a sketch illustrating the manufacture of boards 220b is shown. Boards 220a would be formed in a similar fashion. Several boards 220b are formed form a single sheet of fiberglass stock 530 or other suitable material for making printed circuit boards. As is conventional, traces in the desired pattern are formed on two surfaces of the stock 530, including pads 512 for attachment of lighting elements. Channels, such as 520a and 522b are then milled into the stock 530, thereby forming the desired edges of board 220b. As illustrated, channel 520a has a shape that forms platforms, such as 510a . . . 510c. Score lines 524a and 524b are also cut, but are not cut completely through stock 530. At the completion of all handling steps, the epoxy stock can be broken away along the score lines 524a and 524b, leaving a plurality of printed circuit boards 220b.

Having described one embodiment, numerous alternative embodiments or variations might be made. For example, it was described that lighting elements of different beam angles were used to reduce variations in intensity of illumination at different elevation angles. Other ways might be used to equalize intensity. Because groups of lighting elements can be separately controlled, the intensity from some groups might be increased by giving higher input power to that group. Or, where lights are flashed, some groups might be controlled to stay on longer.

Also, it was described that light emitting diodes are used for the preferred embodiment of the lighting elements. Other light sources might be used. For example, optical fibers might be used to distribute light from the desired locations and in the desired directions.

Further, it was described that the base and substrate elements are manufactured as subassemblies and then connected together to form the illumination system. While such a construction is desirable because it simplifies the manufacturing process, it is not required. It would be possible, for example, to have the lighting elements attached to other kinds of support structures. For example, the support structure might be a unitary member. Alternatively, lighting elements disposed along several rays might be attached to the same member to create subassemblies with more lighting elements than pictured herein.

Additionally, it is described in the preferred embodiment, that printed circuit boards are used. Traditional epoxy fiberglass boards with traces might be used, though such are not the only suitable elements. Other substrates are available to form printed circuit boards, such as glass or ceramic. Additionally, ways other than photoetching can be used to create conductive traces. Deposition techniques can be used. Individual wires might also be attached to a substrate to create an equivalent structure. Further, it is not necessary to achieve the advantages of the invention for the traces to be integral with the substrate of the "printed circuit board."

Also, it was pictured that the diode lighting elements rest on the edge of printed circuit boards 220. It should be appreciated that any mounting arrangement that allows the lighting light to project beyond the edge of the circuit boards 220 could work. Thus, alternative ways of mounting the lighting elements along the edge could be used.

Further, it was described that diodes are soldered to the edges of printed circuit boards. Other methods of mounting the diodes might be used. For example, the diodes might be mounted in sockets.

Therefore, the invention should be limited only by the spirit and scope of the appended claims.

What is claimed is:

1. An optical inspection system having a lighting system and an inspection area, comprising:
   a) a support structure;
   b) a plurality of lighting elements disposed in a planar array with each lighting element having a predetermined spacing from an inspection area, wherein a first portion of the plurality of lighting elements has a predetermined spacing that is greater than the predetermined spacing of a second portion of the plurality of lighting elements and wherein the beam width of the first portion is narrower than the beam width of the second portion.

2. The optical inspection system of claim 1, wherein the support structure comprises a plurality of substrates, each positioned along a line extending from the center of the array.

3. The optical inspection system of claim 2 wherein each of the substrates has an edge with a plurality of lighting elements mounted along each edge.

4. The optical inspection system of claim 3 wherein the substrate comprises a printed circuit board and the lighting elements comprise diodes attached to the printed circuit board.

5. The optical inspection system of claim 4 wherein each of the lighting elements being tilted to face the inspection area.

6. An optical inspection system having a lighting system and an inspection area, comprising:
   a) a support structure;
   b) a plurality of lighting elements disposed in a planar array with each lighting element having a predetermined spacing from an inspection area, wherein a first portion of the plurality of lighting elements bas a predetermined spacing that is greater than the predetermined spacing of a second portion of the plurality of lighting elements and wherein the beam width of the first portion is narrower than the beam width of the second portion;

c) wherein the spacing between the lighting elements and the inspection area exceeds 1.8 mm.

7. An optical inspection system of the type having a plurality of cameras focused on an inspection area and an illumination system illuminating the inspection area, comprising:

a) a base having a planar surface and a plurality of electrically conducting traces;

b) a plurality of lighting elements, with the lighting elements positioned in an array parallel with the planar surface, with the lighting elements emitting light towards the inspection area, the array of lighting elements having a plurality of open areas therein, with a first of the open areas located in the center region of the array and at least a second of the open areas offset from the center;

c) a plurality of cameras directed towards the inspection area, each focused through an open area;

d) wherein the plurality of lighting elements are electronically connected to the plurality of electrically conducting traces, whereby a plurality of lighting modes can be generated by selection of electrical signals applied to the electrically conducting traces.

8. The optical inspection system of claim 7 wherein predetermined ones of the lighting elements have narrower beam angles than others of the lighting elements, whereby the variation of the illumination intensity with respect to elevation angle is reduced.

9. The optical inspection system of claim 7 wherein the base comprises a plurality of substrates, each positioned along a ray emanating from the center region and wherein a portion of the plurality of lighting elements is attached to each of the substrates in subarrays along said ray.

10. The optical inspection system of claim 9 wherein the lighting elements comprise diodes and the substrates comprise boards mounted perpendicular to the planar surface of the base and each of the boards has an edge facing the inspection area, the edge having serrations thereon, with the diodes mounted on the serrations.

11. The optical inspection system of claim 9 wherein each of the lighting elements produces a beam with a beam angle and a first portion of the plurality of lighting elements has a narrower beam angle than a second portion of the plurality of lighting elements which is closer to said point.

12. The optical inspection system of claim 7 wherein the plurality of electrically conducting traces are connected to connectors mounted to the base, whereby the plurality of light emitting elements may be electrically connected to the optical inspection system.

13. The optical inspection system of claim 7 wherein the plurality of electrically conducting traces are routed to allow independent control over lights in regions of the array.

14. The optical inspection system of claim 7 wherein the plurality of cameras is five cameras, with one camera focused through the first of the open areas.

15. A method of manufacturing a printed circuit board using the automated optical inspection system of claim 7, the method comprising:

a) disposing a portion of the printed circuit board being manufactured in the inspection area;

b) selectively activating portions of the lighting elements;

c) forming one or more images of the portion of the printed circuit board using one or more of the plurality of cameras;

d) determining the next processing step for the printed circuit board being manufactured using an analysis of the one or more images.

16. The method of claim 15 wherein forming one or more images comprises forming multiple images using different lighting modes created by sending different patterns of electrical signals through the conducting traces in the base.

* * * * *